United States Patent [19]

Blehm et al.

[11] Patent Number: 4,842,766

[45] Date of Patent: Jun. 27, 1989

[54] SILANE MICROEMULSIONS

[75] Inventors: Lynne M. Blehm; William C. White, both of Midland, Mich.

[73] Assignee: Dow Corning Corporation, Midland, Mich.

[21] Appl. No.: 15,645

[22] Filed: Feb. 17, 1987

[51] Int. Cl.$^4$ ............................................. B01J 13/00
[52] U.S. Cl. .................................. 252/309; 252/312; 514/63; 514/941
[58] Field of Search .................. 514/63, 941; 252/309, 252/312

[56] References Cited

U.S. PATENT DOCUMENTS

| | | | |
|---|---|---|---|
| 3,294,725 | 12/1966 | Findlay et al. | 260/29.2 |
| 3,433,780 | 3/1969 | Cekada et al. | 260/29.2 |
| 3,644,255 | 2/1972 | Thompson | 260/29.1 |
| 3,730,701 | 5/1973 | Isquith et al. | 71/67 |
| 3,730,905 | 5/1973 | Koerner et al. | 252/316 |
| 4,005,030 | 1/1977 | Heckert et al. | 252/140 |
| 4,052,331 | 10/1977 | Dumoulin | 252/312 |
| 4,122,029 | 10/1978 | Gee et al. | 252/309 |
| 4,146,499 | 3/1979 | Rosano | 252/186 |
| 4,374,879 | 2/1983 | Roberts et al. | 523/404 |
| 4,529,758 | 7/1985 | Traver | 524/43 |
| 4,620,878 | 11/1986 | Gee | 106/287.15 |
| 4,631,273 | 12/1986 | Blehm et al. | 514/29 |

FOREIGN PATENT DOCUMENTS

| | | |
|---|---|---|
| 0075990 | 4/1983 | European Pat. Off. . |
| 48908 | 3/1985 | Japan ............ 514/63 |

OTHER PUBLICATIONS

Dow Corning Corp., "Information About Antimicrobial Agents",(1978) 4 p.

Isquith et al., "Surface-Bonded Antimicrobial ACtivity of an Organosilicon Quaternary Ammonium Chloride", Appl. Microbiol., vol. 24(6), (1972), pp. 859-863.

Chemical Abstracts, vol. 85, No. 16, 10-18-76, p. 106, No. 110398y.

Primary Examiner—Matthew A. Thexton
Attorney, Agent, or Firm—James L. De Cesare

[57] ABSTRACT

Clear stable micellar solutions comprising:
(a) a silane represented by the formulae:

$$X_{4-n}Si(RNH_aR'_bY_c)_n \quad (i)$$

where X denotes an alkoxy radical with 1 to 6 carbon atoms, or an alkoxyalkoxy radical with 2 to 8 carbon atoms, or an alkyl radical with 1 to 6 carbon atoms;
Y denotes an acid anion;
n is 1, 2 or 3;
R denotes a divalent hydrocarbon radical with 1 to 6 carbon atoms;
R' denotes alkyl radicals with 1 to 22 carbon atoms; saturated hydrocarbon radicals containing nitrogen, or unsaturated hydrocarbon radicals containing nitrogen;
a is 0, 1 or 2;
b is 0, 1, 2, or 3;
c is 0 or 1; the sum of a+b is 2 or 3 and when the sum of a and b is 3, c is 1, otherwise c is 0;

$$X_{4-n}Si(RPR''_3Y)_n \quad (ii)$$

where X denotes an alkoxy radical with 1 to 6 carbon atoms, or an alkoxyalkoxy radical with 2 to 8 carbon atoms, or an alkyl radical with 1 to 6 carbon atoms, R denotes a divalent hydrocarbon radical with 1 to 6 carbon atoms; R'' denotes an alkyl radical with 1 to 20 carbon atoms, or a phenyl radical, and n is 1, 2, or 3; or $$X_3SiR''' \quad (iii)$$

where X denotes an alkoxy radical with 1 to 6 carbon atoms, or an alkoxyalkoxy radical with 2 to 8 carbon atoms, or an alkyl radical with 1 to 6 carbon atoms and R''' denotes an alkyl radical with 1 to 6 carbon atoms or a phenyl radical; and
(b) a cosurfactant with an HLB of at least 1.

21 Claims, 9 Drawing Sheets

SILANE MICROEMULSIONS

The present invention relates to microemulsions, clear micellar solutions, and clear liquid crystalline solutions stabilized by a combination of a silane and a cosurfactant. These microemulsions and micellar solutions are effective delivery systems for the silane surfactants.

For the purposes of the present application the term "microemulsion" is understood as a stable mixture of a water immiscible oil phase and a water phase. In general, there are at least two types of microemulsions, oil-in-water types and water-in-oil types. In oil-in-water type microemulsions the oil phase is discontinuous with a continuous water phase. In other words the oil phase is comprised of droplets of oil suspended in a continuous water phase. In water-in-oil type microemulsions the water phase exists as discontinuous droplets in a continuous oil phase. Microemulsions of both types are characterized by particle sizes. The size of the discontinuous phases are generally less than 0.150 micron in diameter. Because of the small average particle size microemulsions are clear solutions containing micelles with average particle sizes less than 0.150 micron in diameter. These clear or translucent solutions are particularly stable. They do not separate into distinct oil and water layers with time. Microemulsions are also more stable than standard emulsions made from the same materials, and exhibit greater freeze-thaw stability and ease of formulation than their standard emulsion counterparts. The term "clear mixture", for the purpose of this invention, is understood to encompass micellar solutions, microemulsions, and liquid crystalline solutions, but does not include classic solutions. The term "clear mixtures" is also understood to encompass mixtures which are translucent.

Liquid crystalline solutions are mixtures of at least two components and as many as four components: a surfactant or emulsifier component, a water immiscible component, a water component and a cosurfactant component. The emulsifier or surfactant molecules are arranged in liquid crystalline solutions in such a way as to form relatively large crystal like structures which raise the viscosity of the solution sometimes to the point where the solution appears as a solid. When the dimensions of the crystals are sufficiently small the liquid crystalline solutions are clear or translucent.

Microemulsions have been known for a number of years. In fact, many commercial microemulsion products exist including paste waxes, cutting oils, delivery systems for pesticides, and flavor oil microemulsions.

The term "micellar solutions" for the purposes of the present application is understood to mean solutions with particle sizes of less than 0.150 micron. In general, these include solutions of surfactants and mixtures of surfactants and cosurfactants. Micellar solutions also encompass the aforementioned microemulsions, but also include solutions where only a water phase or an oil phase exist in combination with an emulsifier. The emulsifier molecules in micellar solutions aggregate and orient so as to expose one portion of the molecule to the continuous phase of the solution, and orient the other portion of the molecule towards similar portions of other emulsifier molecules. For instance, in aqueous micellar solutions the emulsifier molecules will orient their hydrophillic portions towards the continuous water phase, and orient their hydrophobic portions towards the interior of the emulsifier micelle.

In general, microemulsions exist as a means for delivering an oil (or other water immiscible component) to a surface in a convenient form. For instance, paste waxes are oil-in-water microemulsions which deliver the wax in a less viscous form to the substrate to be polished than pure wax. Microemulsions of flavor oils are used to deliver flavor to soft drinks. In both cases the primary use of the microemulsion is to deliver the oil to a substrate. Other uses of microemulsions take advantage of the physical properties of specific microemulsions. For instance, microemulsions used as cutting oils are particularly effective lubricants and coolants.

Microemulsions containing organosiloxanes are known in the art. U.S. Pat. No. 3,294,725 issued to Findlay et al. teaches a method of polymerizing polysiloxane precursor molecules by an emulsion method using surface active sulfonic acid catalysts which act as polymerization catalysts and as emulsifiers. Example 24 of the Findlay patent shows how to make a translucent emulsion of polydimethylsiloxane. Findlay does not teach using silanes as emulsifiers for clear microemulsions.

Cekada, et al., U.S. Pat. No. 3,433,780, teaches how to make translucent dispersions of silsesquioxanes of the general formula $$RSiO_{3/2}$$

where R denotes an alkyl radical with 1 to 6 carbon atoms or a phenyl radical Cekada's dispersions have particle sizes in the range of 0.001 to 0.100 micron and contain less than 10 weight percent silsesquioxanes. The silsesquioxanes are resins according to Cekada.

U.S. Pat. No. 4,052,331 issued to Dumoulin teaches a special emulsifier composition which can be used to stabilize polysiloxane oil-in-water microemulsions. The emulsifier composition comprises: n-alkyl monoether of polyethylene glycol; sodium dialkylsulphosuccinate; an acid selected from oleic, linoleic, linolenic, and ricinoleic; and amine. Variation of the composition outside the limits of the invention produces coarse emulsions of polysiloxane and water, rather than microemulsions thereof. Dumoulin's emulsifier compositions do not include silanes.

U.S. Pat. No. 4,146,499 issued to Rosano teaches a method for producing low solids content oil-in-water microemulsions. Rosana's method does not teach the use of silanes in combination with organic surfactants as effective emulsifiers for microemulsions.

U.S. Pat. No. 4,529,758 issued to Travers teaches stable dispersions of silicone resins. Travers's stable resin suspensions do not suggest the use of silanes as suspending agents.

U.S. Pat. No. 4,620,878 issued to Gee teaches a method for making stable microemulsions of polar radical containing polysiloxane oils. Gee teaches using organic emulsifiers in the claimed process.

U.S. Pat. No. 4,631,273 issued to Blehm, et al. teaches using silanes as emulsifiers for stabilizing standard oil-in-water emulsions. The patent does not teach how to make microemulsions.

SUMMARY OF THE INVENTION

The present invention relates to clear compositions comprised of:
(a) a silane represented by the formulae:

$$X_{4-n}Si(RNH_aR'_bY_c)_n \quad \text{(i)}$$

where X denotes an alkoxy radical with 1 to 6 carbon atoms, or an alkoxyalkoxy radical with 2 to 8 carbon atoms, or an alkyl radical with 1 to 6 carbon atoms;
Y denotes an acid anion;
n is 1, 2 or 3;
R denotes a divalent hydrocarbon radical with 1 to 6 carbon atoms;
R' denotes alkyl radicals with 1 to 22 carbon atoms; saturated hydrocarbon radicals containing nitrogen, or unsaturated hydrocarbon radicals containing nitrogen;
a is 0, 1 or 2;
b is 0, 1, 2, or 3;
c is 0 or 1; the sum of a+b is 2 or 3 and when the sum of a+b is 3, c is 1, otherwise c is 0;

$$X_{4-n}Si(RPR''_3Y)_n \quad \text{(ii)}$$

where X denotes an alkoxy radical with 1 to 6 carbon atoms, or an alkoxyalkoxy radical with 2 to 8 carbon atoms, or an alkyl radical with 1 to 6 carbon atoms, R denotes a divalent hydrocarbon radical with 1 to 6 carbon atoms, R'' denotes an alkyl radical with 1 to 20 atoms, or a phenyl radical, and n is 1, 2, or 3; or $$X_3SiR''' \quad \text{(iii)}$$

where X denotes an alkoxy radical with 1 to 6 carbon atoms, or an alkoxyalkoxy radical with 2 to 8 carbon atoms, or an alkyl radical with 1 to 6 carbon atoms and R''' denotes an alkyl radical with 1 to 6 carbon atoms or a phenyl radical;
(b) a cosurfactant compound has an HLB factor of at least 1, in sufficient quantity that when combined with said silane forms a clear mixture at room temperature which can be diluted with water to form a clear micellar solution.

The invention also relates to micellar solutions, oil-in-water and water-in-oil microemulsions, and liquid crystalline solutions made using said clear mixtures.

DETAILED DESCRIPTION OF THE INVENTION

The present invention relates to novel clear mixtures comprised of a silane (a), and a cosurfactant (b). Optionally, the clear mixtures may further comprise a minor portion of water (c) to form clear and stable micellar solutions or liquid crystalline solutions. The clear mixtures of silane and cosurfactant can also be diluted with a major portion of water (d) to form clear, stable micellar solutions, or they can be mixed with a water immiscible oil (e) and then diluted with a minor portion of water to form water-in-oil microemulsions, or diluted with a major portion of water to form clear, stable oil-in-water microemulsions.

Silanes which can be used in the present invention are widely varied in structure and include silanes represented by the formulae:

$$X_{4-n}Si(RNH_aR'_bY_c)_n \quad \text{(i)}$$

wherein X denotes an alkoxy radical with 1 to 6 carbon atoms, or an alkoxyalkoxy radical with 2 to 8 carbon atoms, or an alkyl radical with 1 to 6 carbon atoms;
Y denotes an acid anion; such as a chloride, bromide, iodide, sulfate, or phosphate with the monovalent halide anions being preferred;
n is 1, 2 or 3;
R denotes a divalent hydrocarbon radical with 1 to 6 carbon atoms;
R' denotes alkyl radicals with 1 to 12 carbon atoms; saturated hydrocarbons radicals containing nitrogen, such as

—$CH_2CH_2NH_2$,

—$CH_2CH_2NHCH_3$, or

—$CH_2CH_2N(CH_3)_2$, or unsaturated hydrocarbon radicals containing nitrogen; such as —$CH_2CH_2NHCH_2C_6H_4CHCH_2$;
a is 0, 1 or 2;
b is 0, 1, 2, or 3;
c is 0 or 1; the sum of a+b is 2 or 3, and when the sum of a+b is 3, c is 1, otherwise c is 0;

$$X_{4-n}Si(RPR''_3Y)_n \quad \text{(ii)}$$

where X denotes an alkoxy radical with 1 to 6 carbon atoms, or an alkoxyalkoxy radical with 2 or 8 carbon atoms, or an alkyl radical with 1 or 6 carbon atoms, R denotes a divalent hydrocarbon radical with 1 to 6 carbon atoms, R'' denotes an alkyl radical with 1 to 20 carbon atoms, or a phenyl radical, and n is 1, 2, or 3; or $$X_3SiR''' \quad \text{(iii)}$$

where X denotes an alkoxy radical with 1 to 6 carbon atoms, or an alkoxyalkoxy radical with 2 to 8 carbon atoms, or an alkyl radical with 1 to 6 carbon atoms and R''' denotes an alkyl radical with 1 to 6 carbon atoms or a phenyl radical;

Specific silanes within the scope of the invention are represented by the formulae:

$(CH_3O)_3Si(CH_2)_3N^+(CH_3)_2C_{18}H_{37}Cl^-$, $(CH_3O)_3Si(CH_2)_3N^+(CH_3)_2C_{18}H_{37}Br^-$, $(CH_3O)_3Si(CH_2)_3N^+(C_{10}H_{21})_2CH_3\ Cl^-$, $(CH_3O)_3Si(CH_2)_3N^+(C_{10}H_{21})_2CH_3\ Br^-$, $(CH_3O)_3Si(CH_2)_3N^+(CH_3)_3\ Cl^-$, $(CH_3O)_3SiCH_3$, $(CH_3O)_3SiCH_2CH_2CH_3$, $(CH_3O)_3SiCH_2CH_2CH_2CH_2CH_2CH_3$, $(CH_3O)_3SiC_6H_5$ $(CH_3O)_3SiCH_2CH_2CH_2P^+(C_6H_5)_3\ Cl^-$, $(CH_3O)_3SiCH_2CH_2CH_2P^+(C_6H_5)_3\ Br^-$, $(CH_3O)_3SiCH_2CH_2CH_2P^+(CH_3)_3Cl^-$, $(CH_3O)_3SiCH_2CH_2CH_2P^+(C_6H_{13})_3Cl^-$,

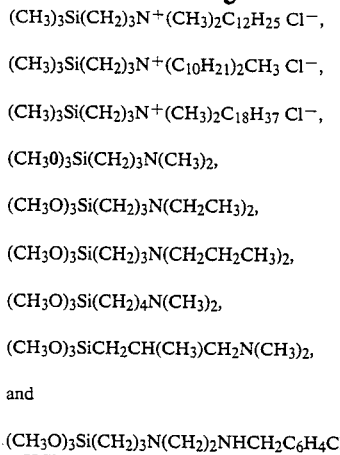

Special precautions must be taken in the preparation of the above mentioned silanes. Although these silanes can be prepared by known methods, or acquired commercially, special care must be taken to remove lower alcohols, such as methanol, ethanol, or propanol, before blending the silane with the cosurfactant. Very often the silanes are commercially available in methanol based solutions. Failure to remove such alcohols will result in the formation of creamy white emulsions which relative to the microemulsions of the present invention are unstable in that they will form separate oil and water phases with time. For purposes of the present invention it is understood that the formulas above represent the formula of the silanes as starting materials. Removing the lower alcohol from the commercial form of the silane may lead to partial hydrolysis of the silane when moisture is present. Therefore it is necessary to strip the methanol from the silane mixture under as dry conditions as possible. While it is preferred to remove the methanol as completely as possible, silanes containing up to 4 weight percent residual methanol can be used successfully to form the clear mixtures of the present invention.

A wide range of cosurfactants can be used in the present invention in order to produce the clear pourable liquids, the clear stable micellar solutions, and the clear stable oil-in-water microemulsions of the present invention. Specifically, polyethylene glycol, ethylene glycol, pentanol, glycerine, and a polyoxyethylene glycol ether of linear alcohols, sold as Tergitol ® 15-S-3 by Union Carbide were used successfully to produce the desired liquids, solutions and microemulsions.

Other cosurfactants which can be used in the present invention are those surfactants which may be soluble in the water immiscible oil used in the particular emulsion. In general, these cosurfactants have an HLB factor of at least 1 and include sorbitan esters of fatty acids with 10 to 22 carbon atoms; polyoxyethylene sorbitol esters of C10 to C22 fatty acids having up to 95 percent ethylene oxide; polyoxyethylene sorbitol esters of C10 to C22 fatty acids; polyoxyethylene derivatives of fatty phenols having 6 to 20 carbon atoms and up to 95 percent ethylene oxide; fatty amino and amide betaines having 10 to 22 carbon atoms, polyoxyethylene condensates of C10 to C22 fatty acids or fatty alcohols having up to 95 percent ethylene oxide; ionic surfactants such as alkylaryl sulfonates with alkyl groups of 6 to 20 carbon atoms; C10 to C20 fatty acid soaps; C10 to C20 fatty sulfates; C10 to C22 alkyl sulfonates; alkali metal salts of dialkyl sulfosuccinates; C10 to C22 fatty amine oxides; fatty imidazolines of C6 to C20; fatty amido sulfobetaines having 10 to 22 carbon atoms; quaternary surfactants such as the fatty ammonium compounds having 10 to 22 carbon atoms; C10 to C22 fatty morpholine oxides; alkali metal salts or carboxylated ethoxylated C10 to C20 alcohols having up to 95 percent ethylene oxide; ethylene oxide condensates of C10 to C22 fatty acids; and alkoxylated siloxane surfactants containing ethylene oxide and/or propylene oxide units; and ethylene oxide condensates of C10 to C22 fatty acid monoesters of glycerines having up to 95 percent ethylene oxide; and mono- or diethanol amides of C10 to C22 fatty acids. Other types of surfactants are known in the art which have an HLB factor greater than or equal to about 1 and which could be used in the practice of the invention. Such surfactants are described in a number of publications including McCutcheon's Detergents and Emulsifiers/North American Edition, 1975, MC Publishing Company, Glen Rock, N.J.

The range of weight ratio of silane to cosurfactant within the scope of the present invention varies with the particular combination of silane and cosurfactant. However, the range for all combinations is the range within which the mixture of the silane and the cosurfactant forms a clear mixture upon thorough mixing. Once a clear or translucent mixture of silane and cosurfactant has been obtained the mixture can be diluted with water to form a clear water-in-oil micellar solution which can then be further diluted to form a clear oil-in-water micellar solution.

Particular combinations of silane and cosurfactant which fall within the scope of the present invention include: 1 to 99 weight parts 3-(trimethoxysilyl)propyldimethyloctadecyl ammonium chloride and 1 to 99 weight parts ethylene glycol; 1 to 99 weight parts 3-(trimethoxysilyl)propyldimethyloctadecyl ammonium chloride and 1 to 99 weight parts propylene glycol; 1 to 99 weight parts 3-(trimethoxysilyl)propyldimethyloctadecyl ammonium chloride and 1 to 99 weight parts glycerol; 1 to 99 weight parts 3-(trimethoxysilyl)propyldimethyloctadecyl ammonium chloride and 1 to 99 weight parts pentanol; and 1 to 99 weight parts 3-(trimethoxysilyl)propyldimethyloctadecyl ammonium chloride and 1 to 99 weight parts of polyethylene glycol ether of linear alcohols sold as Tergitol ® 15-S-3 by Union Carbide.

The clear pourable liquids of the present invention can be diluted with water to form clear micellar solutions, or they can be intermixed with a water immiscible oil and then diluted with water to form stable, clear water-in-oil or oil-in-water type micellar solutions.

In general, the clear micellar solutions are formed by mixing the silane with the cosurfactant. Very often, because of the high viscosity of either the silane or the cosurfactant, or both, one or both have to be heated to liquid form before being intermixed to form the clear mixture of the present invention.

To form the clear micellar solutions of the present invention between about 1 to 99 weight parts of the silane and about 1 to 99 weight parts of the cosurfactant are mixed together to form a clear pourable liquid or a clear microcrystalline mixture. Minor portions of water can be added to this mixture, between 1 to 30 weight parts of water to 99 to 70 parts combined weight of silane and cosurfactant, to form clear micellar solutions. These clear micellar solutions can then be diluted with a major portion of water to form a clear, stable micellar solution where the micelles comprised of the silane and cosurfactant associated together may be visible under a microscope. Typically, it requires at least an equal amount of water to the combined weight of the silane and the cosurfactant, or more, to form these clear stable oil-in-water type micellar solutions. Most preferably clear oil-in-water micellar solutions contain 5 weight percent or less silane compound, while on the other hand water-in-oil types contain 95 weight percent or more silane and cosurfactant.

The clear mixtures comprised of the silane and cosurfactant described herein can also be used to form clear, stable, oil-in-water microemulsions containing water immiscible oils and fluids. Typically, this may require dispersing a water immiscible oil or fluid in the silane and cosurfactant mixture and then dispersing said mixture in a major portion of water. However, the order of addition of the various components has not been found critical to the success of the formation of such microemulsions.

For instance, 40 weight parts of cyclopolydimethylsiloxane of the general formula

where n is 3,4,5,6, or 7, and mixtures, can be dispersed in a clear pourable liquid comprising 10 weight parts silane of the general formula

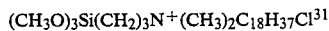

and 10 weight parts propylene glycol. The three component mixture can then be rapidly dispersed in 940 parts of water to form a clear, stable oil-in-water type microemulsion.

The water immiscible oils and fluids within the scope of the present invention include: the aforementioned cyclopolysiloxanes; linear polydiorganosiloxanes of the general formula

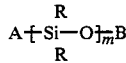

where R denotes an alkyl radical with 1 to 6 carbon atoms, or a phenyl radical, A denotes a hydroxyl or a trimethylsilanol radical, B denotes a hydrogen atom or a trimethylsilyl radical, and m on the average between 1 and 10,000; and other water immiscible hydrocarbons such as mineral oils, petroleum lights, petroleum crude oils, pitch, tar, copolymers, solvents, resins, waxes, waxy polymers, insecticides, flavor oils, perfume oils, and other oils used in cosmetics.

In mixing the components of the invention it should be noted that high shear may have to be applied to the mixtures to ensure codispersion. Thorough dispersion of the components can be achieved by any of the known methods used to emulsify mixtures including ultrasonic methods as well as other high shear techniques.

It is not clear to what degree the alkoxy functional silanes undergo ester exchange or hydrolysis in the clear mixtures of the instant invention, but for the following reasons it is believed the silanes remain in a primarily monomeric state. Silane surfactants of the present invention which have potential silanol functionality (the silanes with alkoxy radicals, for instance) maintain a high degree of silanol functionality in solution despite the presence of water in the mixtures which might otherwise be thought to cause hydrolytic condensation of the silanes. For instance, the micellar solutions comprised of ethylene glycol, water and 3-(trimethoxysilyl)propyldimethyloctadecyl ammonium chloride can be durably bound to substrates to the same degree and with the same effectiveness as state of the art methods employing methanol based solutions of silane diluted in water. Thus, the present invention provides a stable, easily formulateable delivery system for silanes.

While partial hydrolysis of the alkoxy radicals of the silanes does occur in the various forms of the invention, the silanes do not condense to form high molecular weight polymers which are then unable to substantivelly bond to substrates. Because of this unexpected chemical characteristic a particularly useful aspect of the mixtures, etc. is that they are effective delivery systems for said silanes. When one of the mixtures, etc. is put into contact with a substrate, the alkoxy functional silanes condense to form high molecular weight substantive coatings on the surface of the substrate.

Thus the present invention provides a material which effectively delivers a silane to a surface without the disadvantage of also delivering significant amounts of toxic and flammable solvent such as methanol. The silane delivered to the surface or substrate can alter the physical characteristics of that surface. For instance, surfaces can be rendered hydrophobic, hydrophillic, lipophillic, or lipophobic using the mixtures of the present invention.

The actual utilities achievable using the present invention include rendering surfaces antimicrobial, delivering coupling agents to inorganic substrates, delivering color bodies to substrates, delivering antistatic character to fibers, or other substrates, providing corrosion resistant coatings, or delivering nutrients to plants or animals. Essentially any utility achievable by coating a substrate with a hydrolyzable silane can be achieved using the present invention.

The present invention can also be used to deliver water immiscible oils and fluids to substrates. These oils include pesticides, lubricant oils, fluorocarbon oils (which are useful in preventing stains), and oils used in cosmetic formulations.

Specific mixtures which are effective delivery systems for forming antimicrobial coatings are those which contain 3-(trimethoxysilyl)propyldimethyloctadecyl ammonium chloride, 3-(triethoxysilyl)propyldimethyloctadecyl ammonium chloride, 3-(trimethoxysilyl)propyldidecylmethyl ammonium chloride, or similar silyl compounds.

EXAMPLES

The following examples illustrate the present invention without fully exemplifying the full scope of the invention. Comparative examples are presented which demonstrate a number of the critical limits of the invention, or which illustrate the utility of the present invention.

EXAMPLE 1

This example illustrates the wide variety of cosurfactants which operate in conjunction with a 3-(trimethoxysilyl)propyldimethyloctadecyl ammonium chloride to form clear, stable micellar solutions both alone and in further combination with water.

PART 1A

A commercially available sample of 3-(trimethoxysilyl)propyldimethyloctadecyl ammonium chloride obtained from the Dow Corning Corporation as Dow Corning® 5772 Antimicrobial Agent was placed in a beaker with a stirring bar, stirred, heated to about 100° C., and the methanol was removed using a vacuum trap. The heating process boiled away substantially all of the methanol in the Dow Corning® 5772 Antimicrobial Agent product (about 2 to 4 weight percent residual methanol remained) leaving a cream colored wax.

Mixtures comprised of various weight ratios of the cream colored wax and glycerol were made. In order to form the glycerol/3-(trimethoxysilyl)propyldimethyloctadecyl ammonium chloride mixtures the silane had to be heated. Some of the mixtures produced a clear, pourable liquid within the scope of the present invention. The heated silane/cosurfactant was a clear pourable liquid which made intermixing of the two components possible. The characteristics of the mixtures were noted and are reported in Table 1.

TABLE 1

| Wt. silane/wt. glycerol | Observation |
| --- | --- |
| 95/5 | clear |
| 90/10 | clear |
| 80/20 | clear |
| 70/30 | clear |
| 60/40 | clear |
| 50/50 | clear |
| 40/60 | clear |
| 30/70 | two phases |
| 20/80 | two phases |
| 10/90 | liquid crystal |
| 5/95 | liquid crystal |

The clear mixtures were examined with a microscope and micelles were observed. The liquid crystals were confirmed as such by observing the solutions in polarized light and noting the birefringence or lack thereof (solutions containing liquid crystals will display double reflectance, i.e. they will glow when exposed to polarized light). The two phase systems were mixtures of micellar solutions and liquid crystals.

PART 2A

Mixtures similar to those in part 1 were made except that propylene glycol was used in place of glycerol. The observations of the various mixtures are reported in Table 2.

TABLE 2

| Wt. silane/wt. propylene glycol | Observation |
| --- | --- |
| 5/95 | translucent white |
| 10/90 | translucent white |
| 20/80 | clear |
| 30/70 | clear |
| 40/60 | clear |
| 50/50 | clear |
| 60/40 | clear |
| 70/30 | clear |
| 80/20 | clear |
| 90/10 | translucent yellow |

The results indicate that the silane/propylene glycol mixture forms clear pourable liquids at certain ratios. The translucent mixtures were still pourable, but were not as stable to freeze-thaw cycling as the clear liquids.

PART 3A

The method of Part 1 was repeated except that pentanol was used in place of glycerol. The results are reported in Table 3.

TABLE 3

| Wt. silane/wt. pentanol | Observation |
| --- | --- |
| 5/95 | clear |
| 10/90 | clear |
| 20/80 | clear |
| 30/70 | clear |
| 40/60 | clear |
| 50/50 | clear |
| 60/40 | clear |
| 70/30 | clear |
| 80/20 | clear |
| 90/10 | clear |
| 95/5 | clear |

All mixtures of the silane with pentanol produced micellar solutions.

PART 4A

Part 1 was repeated except that ethylene glycol was used in place of glycerol. The results are reported in Table 4.

TABLE 4

| Wt. silane/wt. ethylene glycol | Observation |
| --- | --- |
| 5/95 | clear |
| 10/90 | clear |
| 20/80 | clear |
| 30/70 | clear |
| 40/60 | clear |
| 50/50 | clear |
| 60/40 | clear |
| 70/30 | clear |
| 80/20 | clear |
| 90/10 | clear |

The results demonstrate that a clear pourable micellar liquid can be formed by mixing 3-(trimethoxysilyl)propyldimethyloctadecyl ammonium chloride with ethylene glycol.

PART 5A

Part 1 was repeated once again, this time with the commercially available surfactant Tergitol® 15-S-3, a polyoxyethylene glycol ether of linear alcohols sold by Union Carbide. The results are reported in Table 5.

TABLE 5

| Wt. silane/wt. Tergitol® 15-S-3 | Observation |
| --- | --- |
| 5/95 | clear |
| 10/90 | solid |
| 20/80 | solid |
| 30/70 | solid |
| 40/60 | clear |
| 50/50 | clear |
| 60/40 | clear |
| 70/30 | clear |
| 80/20 | clear |
| 90/10 | clear |

The clear mixtures were observed to be micellar solutions. This shows that a high HLB factor surfactant which is a high molecular weight polymer can be used in combination with a silane surfactant as the emulsifier in clear micellar solutions.

EXAMPLE 2

This example illustrates the variety of silanes which can be used in conjunction with cosurfactants to form clear micellar solutions and clear liquid crystalline solutions. In order to determine whether the various mixtures made in the following examples were classic solutions, micellar solutions, liquid crystals or standard emulsions two techniques were used.

Samples were examined with a microscope for the presence of micelles. Samples which contained micelles and which appeared clear to the eye were labelled microemulsions or micellar solutions.

More viscous solutions were subjected to polarized light. If birefringence occurred in the sample, liquid crystals were present. These samples were also observed with a microscope in order to determine whether the mixture existed in one or multiple phases.

Samples were also visually inspected. Cloudy or milky mixtures were determined to be standard emulsions (emulsions with particle sizes greater than 0.150 micron in diameter).

Clear mixtures observed with a microscope to not have micelles present were subjected to elastic light scattering particle sizing techniques in order to determine if very small sized micelles were present. This procedure was carried out where regions of the phase diagram for a particular system indicated a liquid crystal region adjacent to a clear region which did not have microscope visible micelles.

PART 1B

Various weight ratio mixtures at N-(2-aminoethyl)-3-aminopropyltrimethoxysilane and propylene glycol were made and observed under a microscope. These mixtures were then serially diluted with water and observed. All of the mixtures and dilutions were clear. No micelles could be observed by light microscope.

PART 2B

Various weight ratio mixtures of 3-glycidoxypropyltrimethoxysilane and propylene glycol were made and observed with a microscope. The mixtures were then serially diluted and the dilutions were observed with a microscope in order to determine whether the solutions were micellar solutions or classic solutions. All of the mixtures observed were standard emulsions with particle sizes greater than 0.150 micron in diameter. This is an example of a silane surfactant combination which will not form a clear mixture within the scope of the present invention.

PART 3B

Various weight ratio mixtures of 3-(trimethoxysilyl)propyldidecylmethyl ammonium chloride and propylene glycol were made. The mixtures were observed using a microscope. Mixtures comprised of 3-(trimethoxysilyl)propyldidecylmethyl ammonium chloride and propylene glycol were translucent micellar solutions. A mixture of 81 weight parts 3-(trimethoxysilyl)propyldidecylmethyl ammonium chloride, 9 weight parts propylene glycol and 10 weight parts water was a translucent micellar solution.

PART 4B

Trimethoxysilylpropyltriphenyl phosphonium iodide and propylene glycol were mixed in various weight ratios. These mixtures were then serially diluted with water and were inspected to see if they were micellar solutions or classic solutions. Micellar solutions were observed in both the mixture of the silane and propylene glycol and in the silane/propylene glycol/water mixture. Trimethoxysilylpropyltriphenyl phosphonium iodide can be used with a cosurfactant to form a clear mixture which can be mixed with water to form a translucent micellar solution.

PART 5B 3-(trimethylsilyl)propyldimethyloctadecyl ammonium chloride and propylene glycol were mixed in various weight ratios ranging from 9 weight parts silane to 1 weight part propylene glycol to 1 weight part silane to 9 weight parts propylene glycol. All these mixtures were clear. The observations of the various mixtures are recorded in Table 6.

TABLE 6

| Weight ratio Silane/propylene glycol | Observation |
|---|---|
| 9/1 | liquid crystal |
| 7/3 | clear with liquid crystals |
| 5/5 | clear, low viscosity |
| 3/7 | clear, low viscosity |
| 1/9 | clear, low viscosity |

A light microscope did not indicate that any of the samples contained micelles or liquid crystals. However, the mixtures did form liquid crystalline solutions. Therefore, the 3-(trimethylsilyl)propyldimethyloctadecyl ammonium chloride/propylene glycol mixture is capable of forming clear micellar or liquid crystalline solutions within the scope of the present invention.

PART 6B 3-(trimethoxysilyl)propyltrimethyl ammonium chloride and propylene glycol were combined in various weight ratios. The various mixtures had different viscosities, but all samples were clear and contained micelles or liquid crystals. The observations of the various mixtures are summarized in Table 7.

TABLE 7

| Weight Ratio Silane/Glycol | Observation |
|---|---|
| 9/1 | viscous/amber and clear |
| 7/3 | viscous/amber and clear |
| 5/5 | less viscous/amber and clear |
| 3/7 | clear |
| 1/9 | clear |

Thus the combination of 3-(trimethoxysilyl)propyltrimethyl ammonium chloride and propylene glycol form the clear micellar or liquid crystalline solutions of the present invention.

PART 7B 3-(trimethoxysilyl)propyldimethylamine and propylene glycol were mixed in various weight ratios. All of the mixtures were clear. Microscopic observation revealed the samples contained liquid crystals and micelles. This composition is within the scope of the present invention.

EXAMPLE 3

This example illustrates that the clear mixtures formed in Example 1 are easily diluted to form high and low solids content micellar or liquid crystalline solutions which are stable, and which can be easily formulated with other materials.

PART 1C

The 3-(trimethoxysilyl)propyldimethyloctadecyl ammonium chloride/propylene glycol mixtures of Example 1 Part 1 were serially diluted with water and mixed. The resulting solutions were observed with a microscope and in the presence of polarized light in order to determine whether the solutions contained micelles, liquid crystals, or whether the solutions were present in two phases. The viscosity of the solutions were noted and based upon the three observations each serially diluted sample was described as either a micellar solution, a classic solution, an emulsion, a liquid crystal phase, or a combination thereof. The results are summarized in FIG. 1.

FIG. 1 demonstrates that the various weight ratio mixtures of 3-(trimethoxysilyl)propyldimethyloctadecyl ammonium chloride and propylene glycol can be diluted with water to form clear stable micellar solutions with 10 weight percent solids (the total weight of the silane and the propylene glycol). This mixture can also be diluted with a minor portion of water to form the high solids content clear micellar solutions or high solids content clear liquid crystalline solutions.

PART 2C

A phase diagram for the system containing 3-(trimethoxysilyl)propyldimethyloctadecyl ammonium chloride, glycerol and water was generated using the methods of Part 1C. The phase diagram is reproduced in FIG. 2, and shows that the mixtures of 3-(trimethoxysilyl)propyldimethyloctadecyl ammonium chloride and glycerol can be diluted with water to form low solids contents micellar solutions. The phase diagram also shows that the mixtures can be diluted with minor portions of water to form clear stable low solids content micellar solutions or liquid crystalline solutions.

PART 3C

Mixtures of 3-(trimethoxysilyl)propyldimethyloctadecyl ammonium chloride and a polyoxyethylene glycol ether of linear alcohols sold as Tergitol ® 15-S-3 by Union Carbide were made in various weight ratios and were serially diluted with water. The various samples were observed as in part 1C and a phase diagram for the three component system was made, the results of which are reproduced in FIG. 3. FIG. 3 shows that mixtures of 3-(trimethoxysilyl)propyldimethyloctadecyl ammonium chloride and Tergitol ® 15-S-3 can be diluted to form clear, stable micellar solutions with 0 to 5 weight percent solids. The mixtures can also be diluted with minor portions of water, between 1 and 25 weight percent, to form clear high solids content micellar solutions or liquid crystalline solutions.

PART 4C

Mixtures of 3-(trimethoxysilyl)propyldimethyloctadecyl ammonium chloride and pentanol in various weight ratios were made, serially diluted with water, and each aliquot was observed per the methods of Part 1C. The phase diagram is reproduced in FIG. 4 and shows that mixtures of 3-(trimethoxysilyl)propyldimethyloctadecyl ammonium chloride and pentanol can be diluted with water to form clear, stable micellar solutions with 0 to about 10 weight percent solids contents.

The mixtures will also form high solids content micellar and liquid crystalline solutions.

PART 5C

Mixtures of 3[2(vinyl benzylamino)ethylamino]propyltrimethoxysilane and propylene glycol of various weight ratios were made and serially diluted with water. The various aliquots were observed as in Part 1C. The results showed that the various mixtures could be diluted to form clear, stable micellar solutions of 3[2(vinyl-benzylamino)ethylamino]propyltrimethoxysilane and propylene glycol with about 10 weight percent solids, or less.

PART 6C

Mixtures of methyltrimethoxysilane and propylene glycol were made in various weight ratios and serially diluted with water. The various aliquots were observed as per Part 1C. The results demonstrated that mixtures of methyltrimethoxysilane and propylene glycol can be diluted with water to form stable, clear micellar solutions with solids contents in the 0 to 10 weight percent range. These mixtures can also form high solids content micellar solutions or liquid crystalline solutions.

PART 7C

Mixtures of 3-(trimethoxysilyl)propyldidecylmethyl ammonium chloride and propylene glycol were made in various weight ratios and serially diluted with water. The various aliquots were observed as per Part 1C. The results demonstrated that mixtures of 3-(trimethoxysilyl)propyldidecylmethyl ammonium chloride and propylene glycol can be diluted with water to form stable, clear micellar solutions with solids contents in the 0 to 10 weight percent range.

PART 8C

Mixtures of trimethoxysilylpropyltriphenyl phosphonium iodide and propylene glycol were made in various weight ratios and serially diluted with water. The various aliquots were observed as per Part 1C. The results demonstrated that mixtures of trimethoxysilylpropyltriphenyl phosphonium iodide and propylene glycol can be diluted with water to form stable, clear micellar solutions with solids contents in the 0 to 10 weight percent range.

EXAMPLE 4

This example illustrates the ability of the present invention to form oil-in-water microemulsions using hexane as the water immiscible liquid. Various weight ratio mixtures of propylene glycol and 3-(trimethoxysilyl)propyldimethyloctadecyl ammonium chloride were made. These two component mixtures were serially diluted with water and the aliquots were observed by the methods of Example 3, Part 1C. To each of the resultant mixtures of propylene glycol, 3-(trimethoxysilyl)propyldimethyloctadecyl ammonium chloride and water, hexane was added in order to produce mixtures with 10 weight percent, 30 weight percent, 50 weight percent, 70 weight percent and 90 weight percent hexane. Phase diagrams for these certain weight percentages of hexane mixtures were made and are reproduced in FIGS. 5, 6, 7, 8, and 9. The phase diagrams demonstrate that stable, clear oil-in-water and water-in-oil microemulsions can be made using 3-(trimethoxysilyl)propyldimethyloctadecyl ammonium chloride and propylene glycol as the emulsifier.

EXAMPLE 5

This example demonstrates that microemulsions stabilized by 3-(trimethoxysilyl)propyldimethyloctadecyl ammonium chloride and ethylene glycol are effective delivery systems for durable antimicrobial surface treatments which are functionally equivalent and as effective as state of the art treatments.

The state of the art treatment methods employ commercially available methanolic solutions of 3-(trimethoxysilyl)propyldimethyloctadecyl ammonium chloride or 3-(trimethoxysilyl)propyldidecylmethyl ammonium chloride. These solutions are then diluted with water to 0.5 to 3 weight percent silane concentrations in which substrates are immersed in order to treat such substrates.

Various levels of a mixture of 3-(trimethoxysilyl)propyldimethyloctadecyl ammonium chloride and ethylene glycol diluted with water to about 0 to 5 weight percent silane were applied to a variety of fabrics including polyester, cotton and nylon. Similar samples of the same fabric were treated with a methanol based solution of 3-(trimethoxysilyl)propyldimethyloctadecyl ammonium chloride diluted with water at the same silane concentrations. The surface level treatment as applied to the fabrics was the same in both cases.

The antimicrobial and fungicidal properties of the treated fabrics were measured by accepted methods. For instance, the antimicrobial activity of the treated fabric was tested by a method based upon AATCC Test Method 100. The fungicidal activity of the treated fabric was tested by a method based on AATCC Test Method 50.

On all three types of fabric the method employing the present invention was as effective in creating an antimicrobial surface as the state of the art treatment method employing methanol based solutions of 3-(trimethoxysilyl)propyldimethyloctadecyl ammonium chloride diluted with water.

Figure 1:
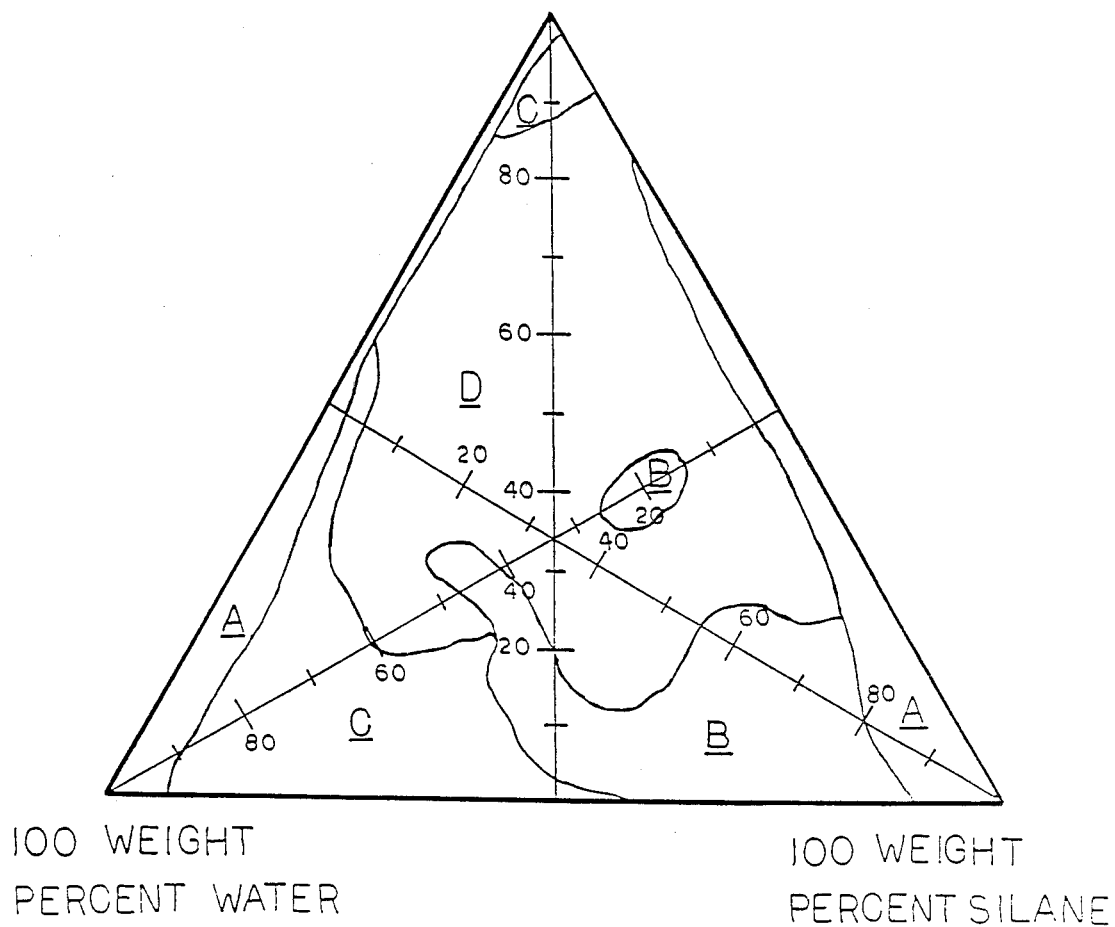
FIG. 1 is the phase diagram for mixtures of 3-(trimethoxysilyl)propyldimethyloctadecyl ammonium chloride, propylene glycol, and water. Regions labelled "A" denote mixtures that formed clear micellar solutions. Regions labelled "B" denote regions where clear viscous solutions of liquid crystals formed. Regions labelled "C" denote regions where standard, creamy emulsions formed. "D" labelled regions denote mixtures that separated into two components.
Figure 2:
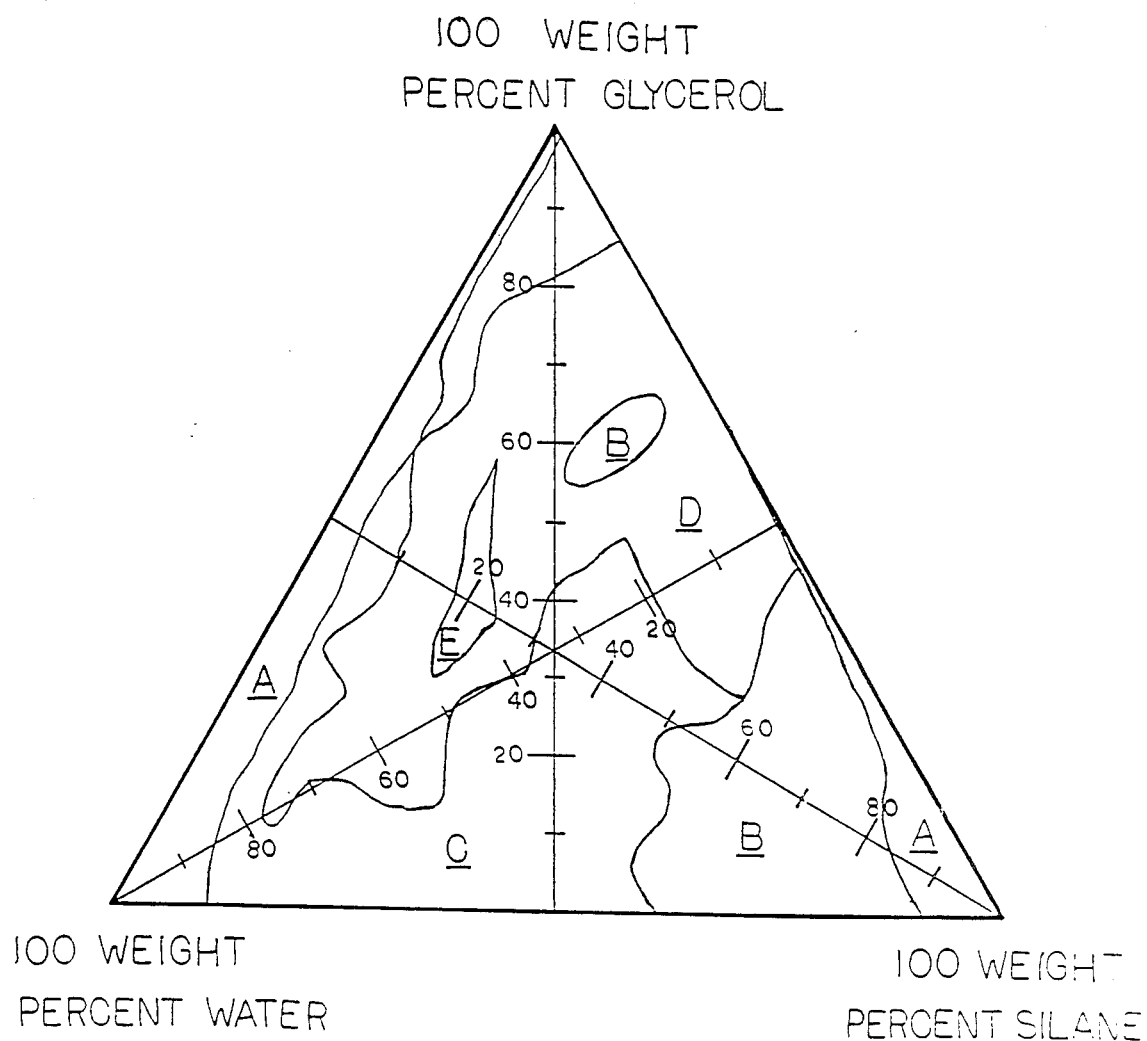
FIG. 2 is the phase diagram for mixtures of 3-(trimethoxysilyl)propyldimethyloctadecyl ammonium chloride, glycerol, and water. Regions labelled "A" denote mixtures that formed clear micellar solutions. Regions labelled "B" denote regions where clear viscous solutions of liquid crystals formed. Regions labelled "C" denote regions where standard, creamy emulsions formed. "D" labelled regions denote mixtures that separated into two components. Regions labelled "E" denote mixtures which separated into three components.
Figure 3:
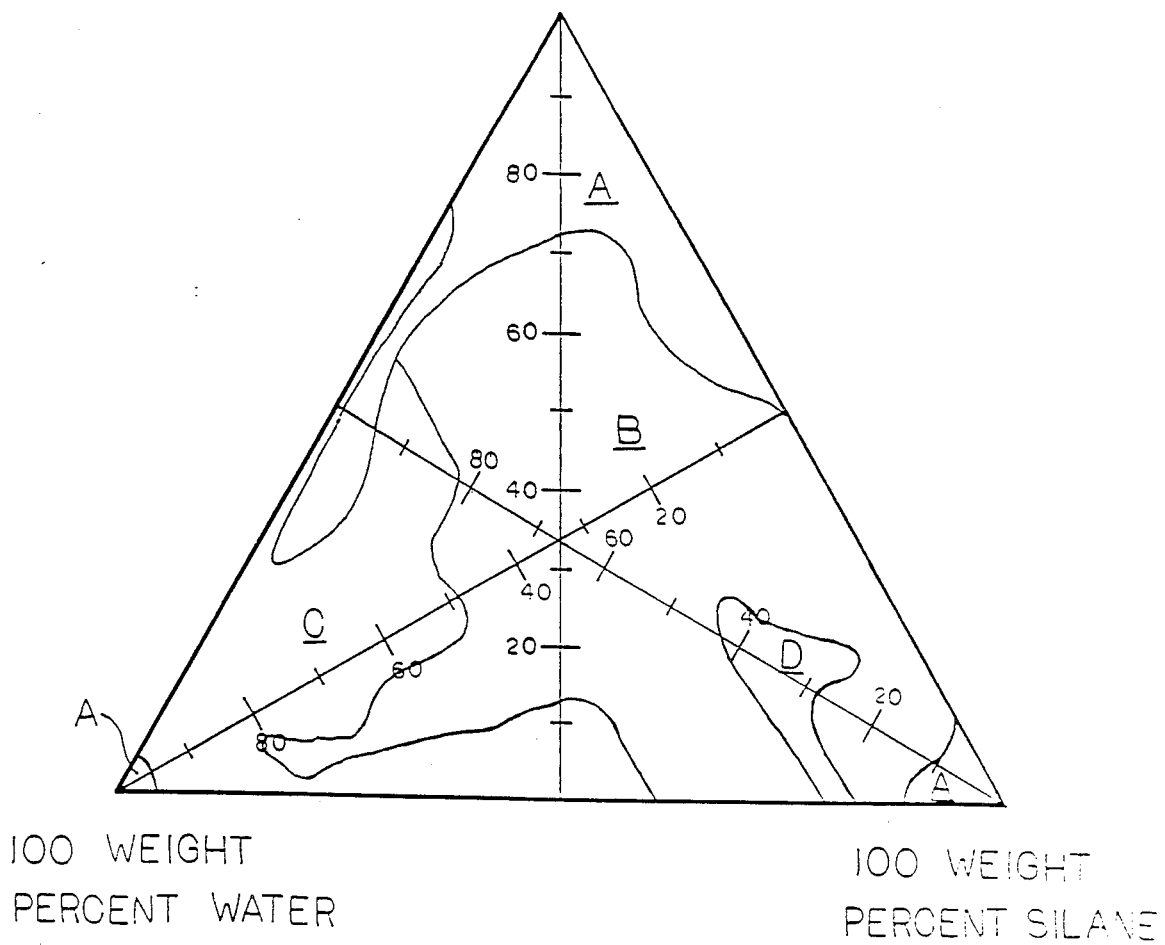
FIG. 3 is the phase diagram for mixtures of 3-(trimethoxysilyl)propyldimethyloctadecyl ammonium chloride, a high molecular weight polyoxyethylene glycol ether of linear alcohols sold as Tergitol® 15-S-3 by Union Carbide, and water. Regions labelled "A" denote mixtures that formed clear micellar solutions. Regions labelled "B" denote regions where clear viscous solutions of liquid crystals formed. Regions labelled "C" denote regions where standard, creamy emulsions formed. "D" labelled regions denote mixtures that separated into two components.
Figure 4:
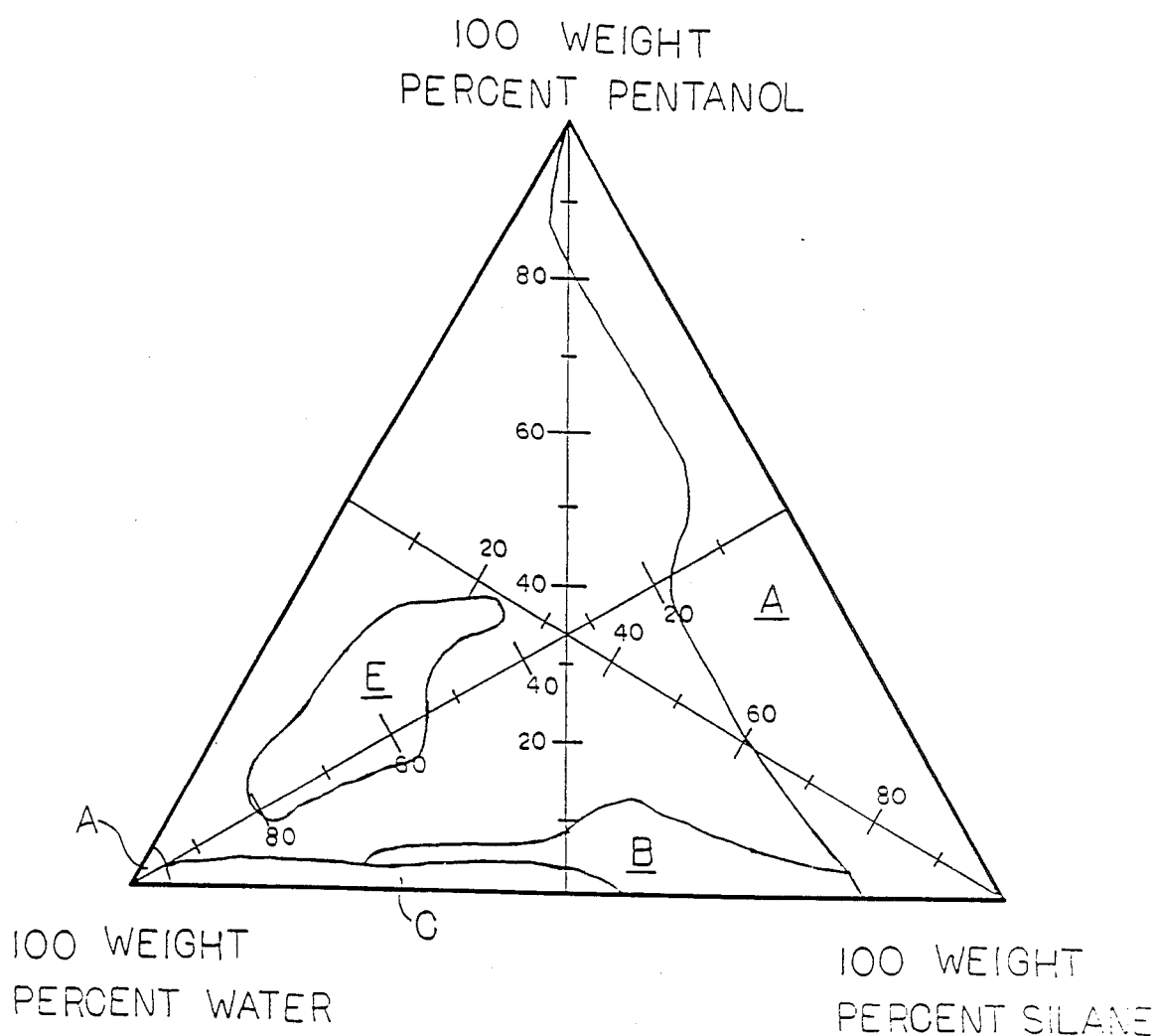
FIG. 4 is the phase diagram for mixtures of 3-(trimethoxysilyl)propyldimethyloctadecyl ammonium chloride, pentanol, and water. Regions labelled "A" denote mixtures that formed clear micellar solutions. Regions labelled "B" denote regions where clear viscous solutions of liquid crystals formed. Regions labelled "C" denote regions where standard, creamy emulsions formed. "D" labelled regions denote mixtures that separated into two components. Regions labelled "E" separated into three components.
Figure 5:
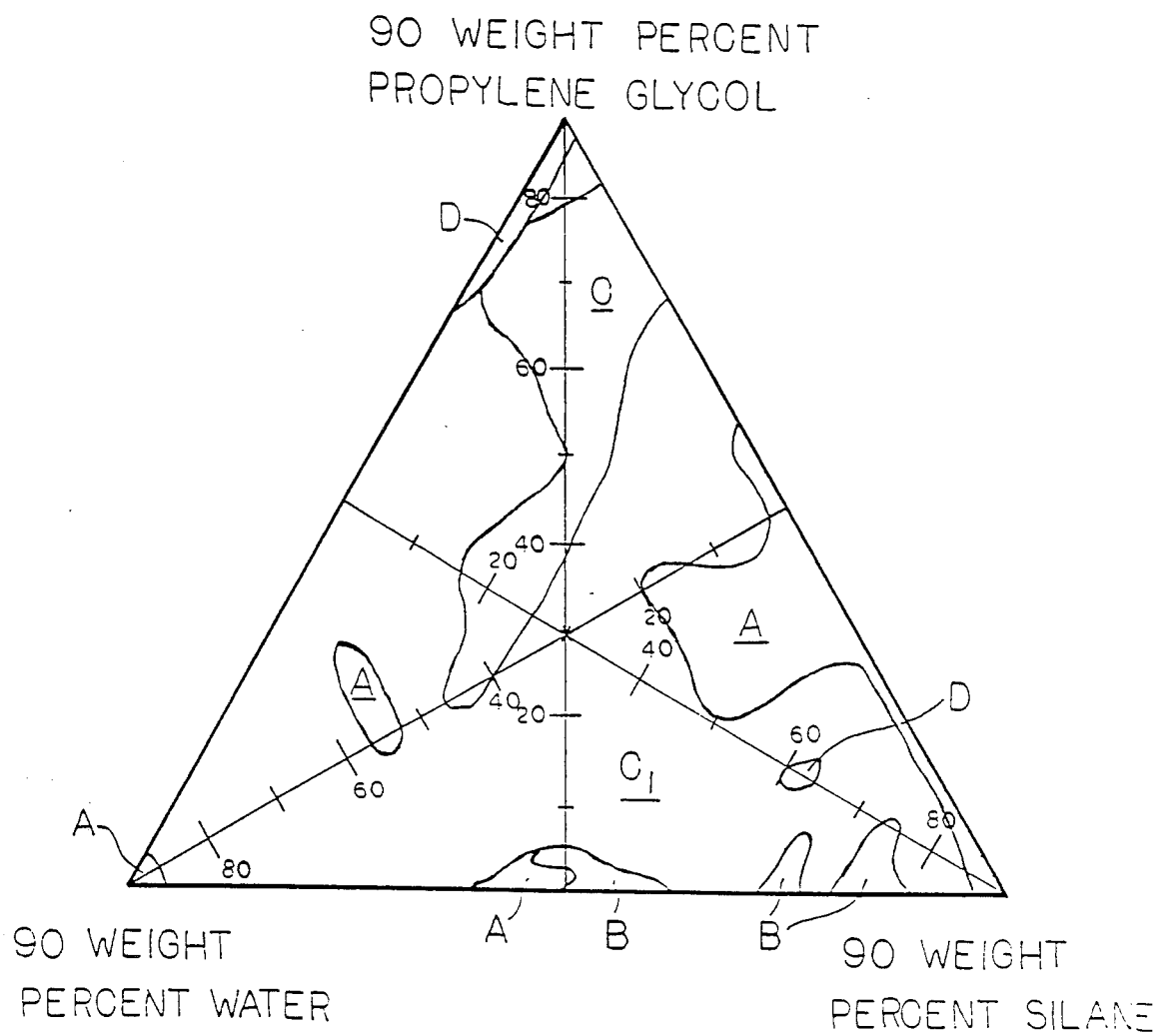
FIG. 5 is the phase diagram for mixtures of various weights of 3-(trimethoxysilyl)propyldimethyloctadecyl ammonium chloride, propylene glycol, and water with 10 weight percent of the immiscible liquid, hexane. Regions labelled "A" denote mixtures that formed clear micellar solutions. Regions labelled "B" denote regions where clear viscous solutions of liquid crystals formed. Regions labelled "C" denote regions where standard, creamy emulsions formed. "D" labelled regions denote mixtures that separated into two components.
Figure 6:
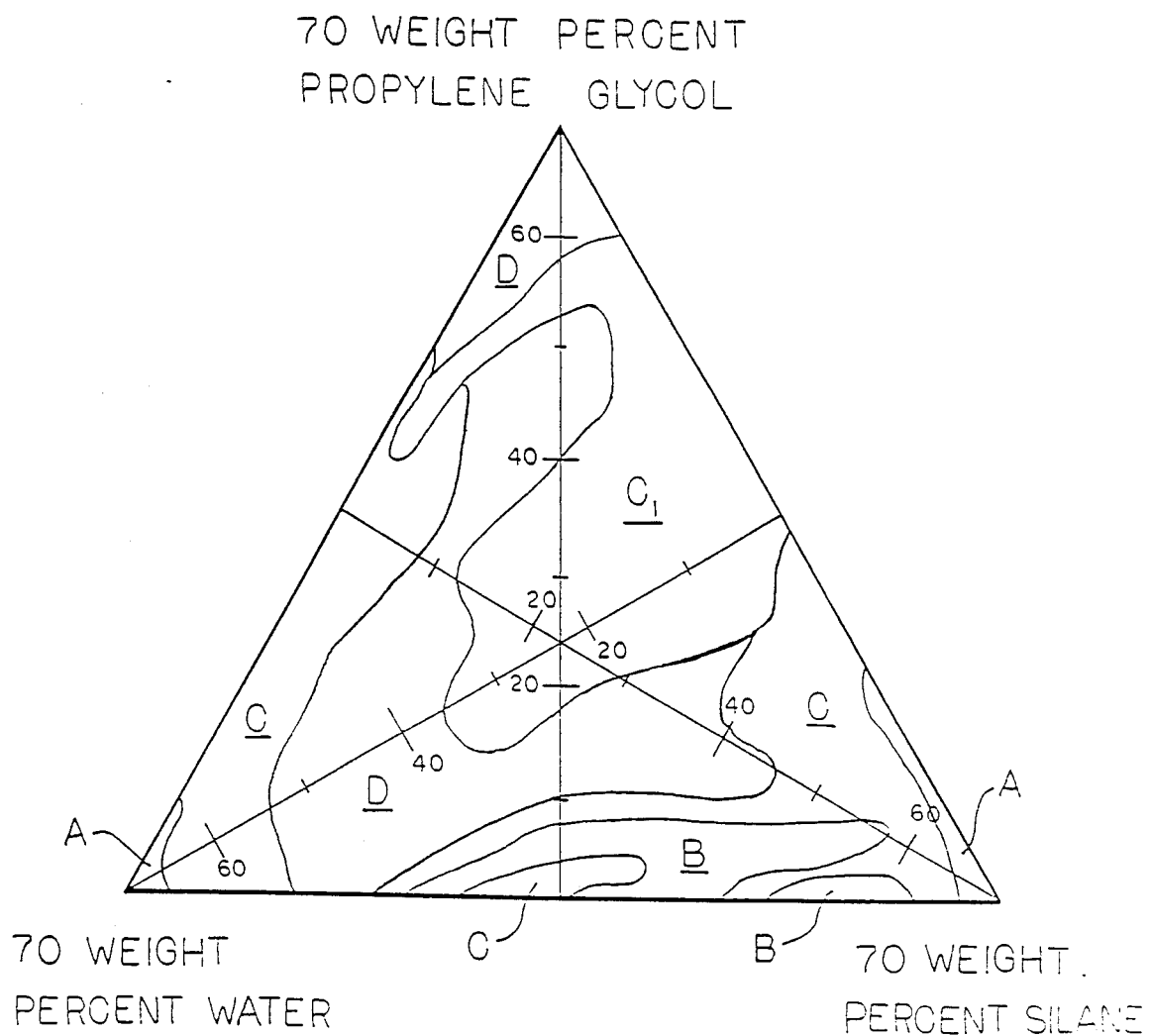
FIG. 6 is the phase diagram for mixtures of various weights of 3-(trimethoxysilyl)propyldimethyloctadecyl ammonium chloride, propylene glycol, and water with 30 weight percent of the water immiscible liquid, hexane.
Figure 7:
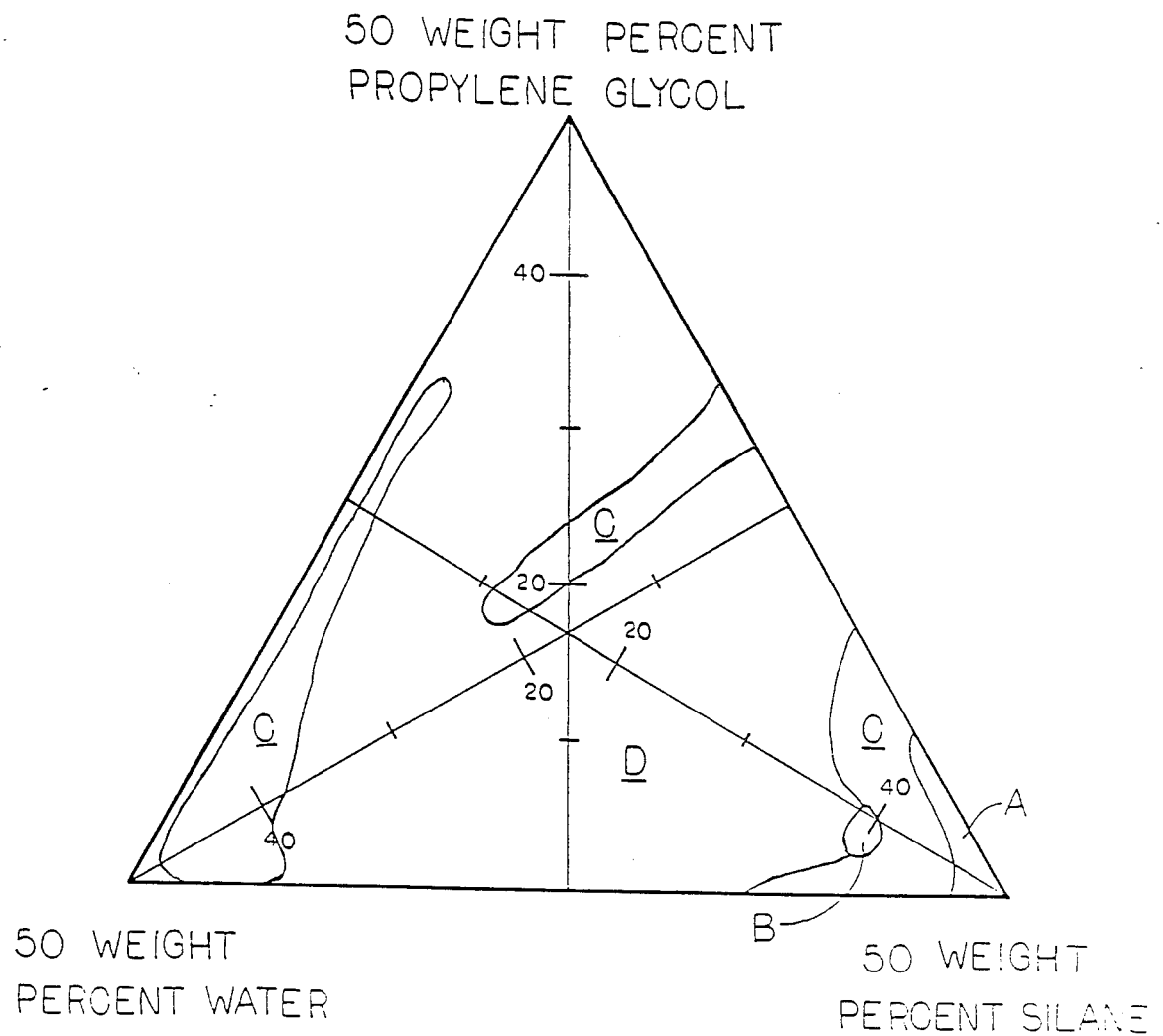
FIG. 7 is the same mixtures with 50 weight percent hexane.
Figure 8:
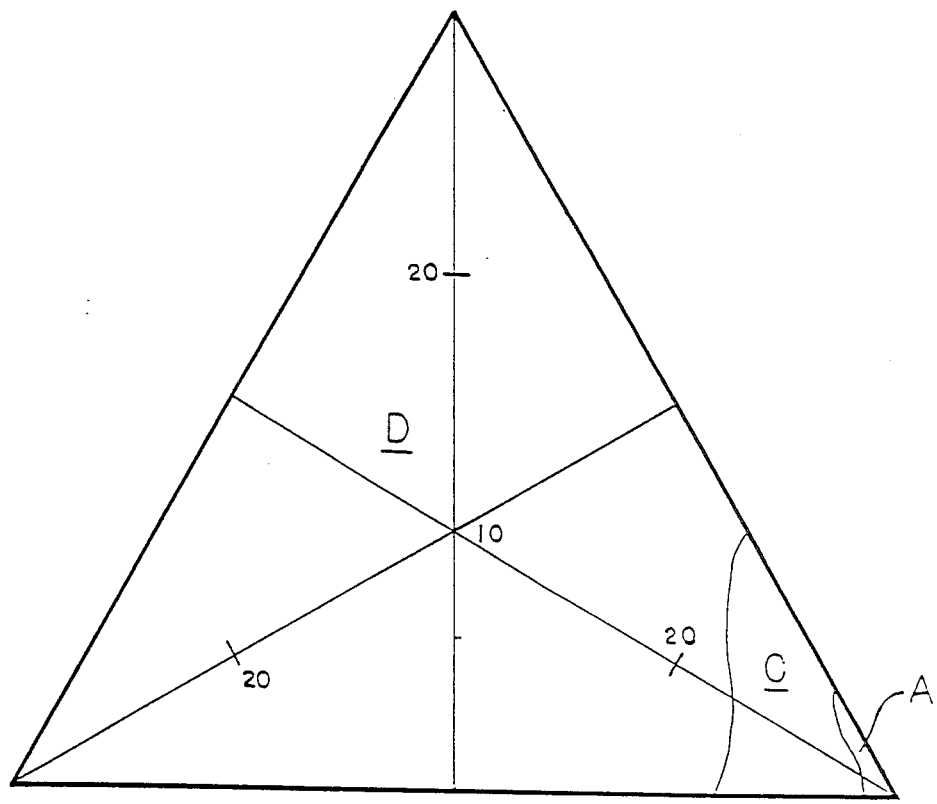
FIG. 8 is with 70 weight percent hexane and FIG. 9 is with 90 weight percent hexane. Regions labelled "A" denote mixtures that formed clear micellar solutions. Regions labelled "B" denote regions where clear viscous solutions of liquid crystals formed. Regions labelled "C" denote regions where standard, creamy emulsions formed. "D" labelled regions denote mixtures that separated into two components. Regions labelled "E" separated into three components.
Figure 9:
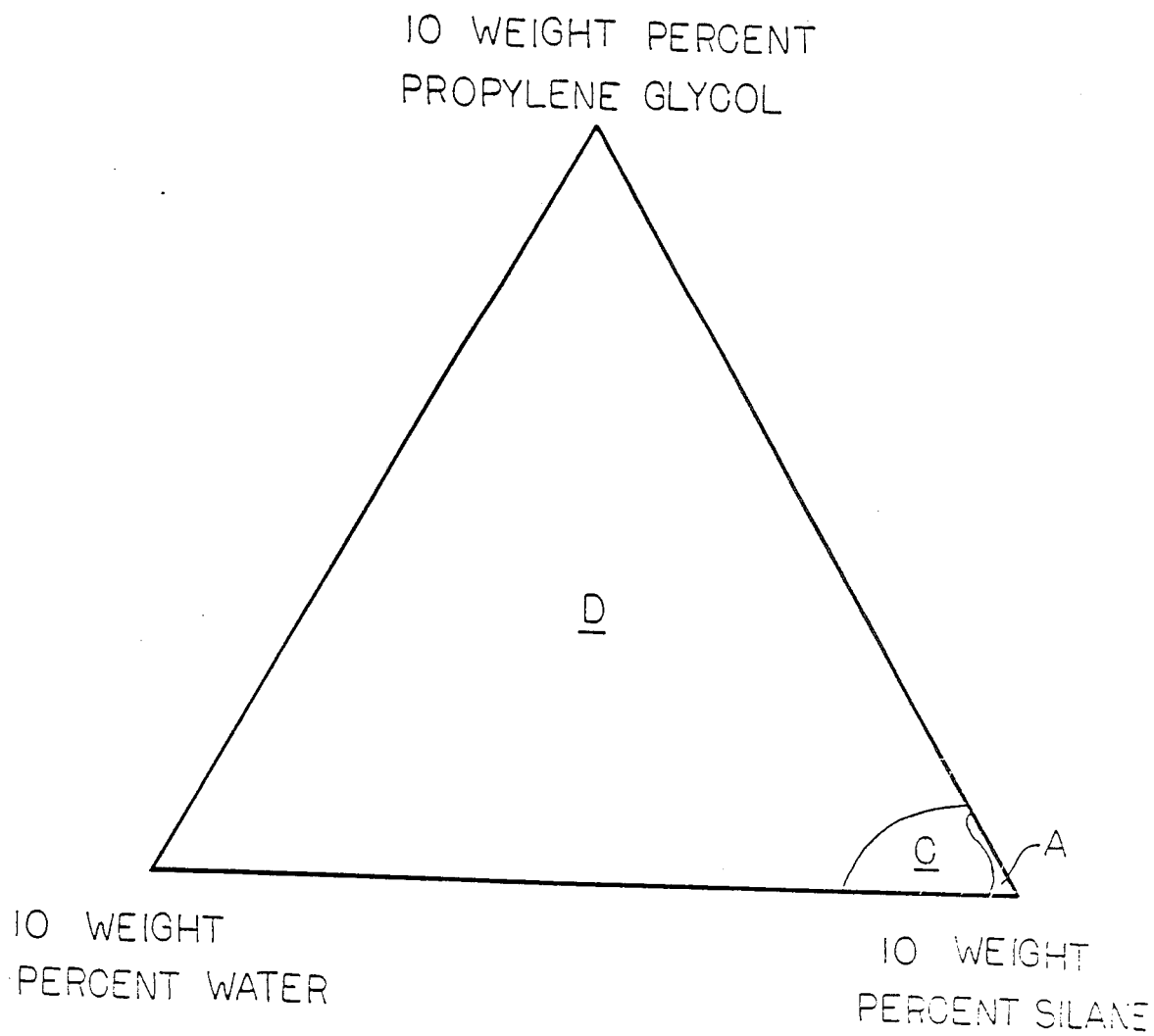

What is claimed is:

1. A clear stable liquid crystalline solution comprising (a) a silane represented by the formulae:

$$X_{4-n}Si(RNH_aR'_bY_c)_n \qquad (i)$$

where X denotes an alkoxy radical with 1 to 6 carbon atoms, or an alkoxyalkoxy radical with 2 to 8 carbon atoms, or an alkyl radical with 1 to 6 carbon atoms;

Y denotes an acid anion;

n is 1, 2 or 3;

R denotes a divalent hydrocarbon radical with 1 to 6 carbon atoms;

R' denotes alkyl radicals with 1 to 22 carbon atoms; saturated hydrocarbon radicals containing nitrogen, or unsaturated hydrocarbon radicals containing nitrogen;

a is 0, 1 or 2;

b is 0, 1, 2, or 3;

c is 0 or 1; the sum of a+b is 2 or 3, and when the sum of a+b is 3, c is 1, otherwise c is 0;

$$X_{4-n}Si(RPR''_3Y)_n \qquad (ii)$$

where X denotes an alkoxy radical with 1 to 6 carbon atoms, or an alkoxyalkoxy radical with 2 to 8 carbon atoms, or an alkyl radical with 1 to 6 carbon atoms, R denotes a divalent hydrocarbon radical with 1 to 6 carbon atoms, R" denotes an alkyl radical with 1 to 20 carbon atoms, or a phenyl radical, and n is 1, 2, or 3; or $$X_3SiR'''  \quad (iii)$$

where X denotes an alkoxy radical with 1 to 6 carbon atoms, or an alkoxyalkoxy radical with 2 to 8 carbon atoms, or an alkyl radical with 1 to 6 carbon atoms and R''' denotes an alkyl radical with 1 to 6 carbon atoms or a phenyl radical;
(b) cosurfactant compound which has an HLB factor of at least 1 and which when combined with said silane forms a clear liquid crystalline solution at room temperature when mixed with water;
(c) sufficient water to form a clear liquid crystalline solution with a mixture of (a) and (b).

2. A clear stable oil-in-water microemulsion comprising
(a) a silane containing less than about four weight percent residual methanol represented by the formulae;

$$X_{4-n}Si(RNH_aR'_bY_c)_n \quad (i)$$

where X denotes an alkoxy radical with 1 to 6 carbon atoms, or an alkoxyalkoxy radical with 2 to 8 carbon atoms, or an alkyl radical with 1 to 6 carbon atoms;
Y denotes an acid anion;
n is 1, 2 or 3;
R denotes a divalent hydrocarbon radical with 1 to 6 carbon atoms;
R' denotes alkyl radicals with 1 to 12 carbon atoms; saturated hydrocarbon radicals containing nitrogen, or unsaturated hydrocarbon radicals containing nitrogen;
a is 0, 1 or 2;
b is 0, 1, 2, or 3;
c is 0 or 1; the sum of a+b is 2 or 3 and when the sum of a+b is 3, c is 1, otherwise c is 0;

$$X_{4-n}Si(RPR''_3Y)_n \quad (ii)$$

where X denotes an alkoxy radical with 1 to 6 carbon atoms, or an alkoxyalkoxy radical with 2 to 8 carbon atoms, or an alkyl radical with 1 to 6 carbon atoms, R denotes a divalent hydrocarbon radical with 1 to 6 carbon atoms, R" denotes an alkyl radical with 1 to 20 carbon atoms, or a phenyl radical, and n is 1, 2, or 3; or $$X_3SiR''' \quad (iii)$$

where X denotes an alkoxy radical with 1 to 6 carbon atoms, or an alkoxyalkoxy radical with 2 to 8 carbon atoms, or an alkyl radical with 1 to 6 carbon atoms and R''' denotes an alkyl radical with 1 to 6 carbon atoms or a phenyl radical; and
(b) cosurfactant compound which has an HLB factor of at least 1, and which when combined with said silane forms a clear mixture at room temperature when mixed with water;
(c) sufficient water to form a clear oil-in-water microemulsion with a mixture of (a) and (b), and a water immiscible oil; and
(d) sufficient water immiscible oil to form a clear stable oil-in-water microemulsion when combined with (a), (b) and (c).

3. The composition of claim 2 where the silane is chosen from the group consisting of $(CH_3O)_3Si(CH_2)_3N^+(CH_3)_2C_{18}H_{37}Cl^-$, $(CH_3O)_3Si(CH_2)_3N^+(CH_3)_2C_{18}H_{37}Br^-$, $(CH_3O)_3Si(CH_2)_3N^+(C_{10}H_{21})_2CH_3Cl^-$, $(CH_3O)_3Si(CH_2)_3N^+(C_{10}H_{21})_2CH_3Br^-$, and $(CH_3O)_3Si(CH_2)_3N^+(CH_3)_3Cl^-$.

4. The composition of claim 2 wherein said silane is chosen form the group consisting of $(CH_3O)_3SiCH_3$, $(CH_3O)_3SiCH_2CH_2CH_3$, $(CH_3O)_3SiCH_2CH_2CH_2CH_2CH_2CH_3$, and $(CH_3O)_3SiC_6H_5$.

5. The composition of claim 2 wherein said silane is chosen from the group consisting of $(CH_3O)_3SiCH_2CH_2CH_2P^+(C_6H_5)_3Cl^-$, $(CH_3O)_3SiCH_2CH_2CH_2P^+(C_6H_5)_3Br^-$, $(CH_3O)_3SiCH_2CH_2CH_2P^+(CH_3)_3Cl^-$, and $(CH_3O)_3SiCH_2CH_2CH_2P^+(C_6H_{13})_3Cl^-$.

6. The composition of claim 2 wherein said silane is chosen form the group consisting of $(CH_3O)_3Si(CH_2)_3N^+(CH_3)_2C_{12}H_{25}Cl^-$, $(CH_3O)_3Si(CH_2)_3N^+(C_{10}H_{21})_2CH_3Cl^-$, and $(CH_3O)_3Si(CH_2)_3N^+(CH_3)_2C_{18}H_{37}Cl^-$.

7. The clear mixture of claim 2 wherein the silane is 3-(trimethoxysilyl)propyldimethyloxtadecyl ammonium chloride (a) and the cosurfactant (b) is propylene glycol and (a) is present from 1 to 99 parts by weight, and (b) is present from 1 to 99 parts by weight.

8. The clear mixture of claim 2 wherein the silane is 3-(trimethoxysilyl)propyldimethyloxtadecyl ammonium chloride (a) and the cosurfactant (b) is ethylene glycol and (a) is present from 1 to 99 parts by weight, and (b) is present from 1 to 99 parts by weight.

9. The clear mixture of claim 2 wherein the silane is 3-(trimethylsilyl)propyldimethyloctadecyl ammonium chloride (a) and the cosurfactant (b) is glycerol and (a) is present from 1 to 99 parts by weight, and (b) is present form 1 to 99 parts by weight.

10. The clear mixture of claim 2 wherein the silane is 3-(trimethoxysilyl)propyldimethyloctadecyl ammonium chloride (a) and the cosurfactant (b) is pentanol and (a) is present from 1 to 99 parts by weight, and (b) is present from 1 to 99 parts by weight.

11. The clear mixture of claim 2 wherein the silane is 3-(trimethoxysilyl)propyldimethyloctadecyl ammonium chloride (a) and the cosurfactant (b) is a polyoxyethylene glycol and (a) is present from 1 to 99 parts by weight, and (b) is present from 1 to 99 parts by weight.

12. The clear mixture of claim 2 wherein the silane is 3-(trimethoxysilyl)propyldimethyloctadecyl ammonium chloride (a) and the cosurfactant (b) is decanol and (a) is present from 1 to 99 parts by weight, and (b) is present from 1 to 99 parts by weight.

13. A clear stable water-in-oil microemulsion comprising
(a) a silane containing less than about four weight percent residual methanol represented by the formulae:

$$X_{4-n}Si(RNH_aR'_bY_c)_n \quad (i)$$

where X denotes an alkoxy radical with 1 to 6 carbon atoms, or an alkoxyalkoxy radical with 2 to 8 carbon atoms, or an alkyl radical with 1 to 6 carbon atoms;
Y denotes an acid anion;
n is 1, 2 or 3;
R denotes a divalent hydrocarbon radical with 1 to 6 carbon atoms;
R' denotes alkyl radicals with 1 to 22 carbon atoms; saturated hydrocarbon radicals containing nitrogen, or unsaturated hydrocarbon radicals containing nitrogen;
a is 0, 1 or 2;
b is 0, 1, 2, or 3;
c is 0 or 1; the sum of a+b is 2 or 3 and when the sum of a+b is 3, c is 1, otherwise c is 0;

$$X_{4-n}Si(RPR''_3Y)_n \quad (ii)$$

where X denotes an alkoxy radical with 1 to 6 carbon atoms, or an alkoxyalkoxy radical with 2 to 8 carbon atoms, or an alkyl radical with 1 to 6 carbon atoms, R denotes a divalent hydrocarbon radical with 1 to 6 carbon atoms, R" denotes an alkyl radical with 1 to 20 carbon atoms, or a phenyl radical, and n is 1, 2, or 3; or $$X_3SiR''' \quad (iii)$$

where X denotes an alkoxy radical with 1 to 6 carbon atoms, or an alkoxyalkoxy radical with 2 to 8 carbon atoms, or an alkyl radical with 1 to 6 carbon atoms and R''' denotes an alkyl radical with 1 to 6 carbon atoms or a phenyl radical;
(b) cosurfactant compound which has an HLB factor of at least 1, and which when combined with said silane forms a clear mixture at room temperature when mixed with water;
(c) sufficient water to form a clear water-in-oil microemulsion with a mixture of (a) and (b), and a water immiscible oil; and
(d) sufficient water immiscible oil to form a clear stable water-in-oil microemulsion when combined with (a), (b) and (c).

14. The composition of claim 13 wherein said silane is $(CH_3O)_3Si(CH_2)_3NH(CH_2)_2NHCH_2C_6H_4CHCH_2$ HCl.

15. The composition of claim 13 wherein said silane is chosen from the group consisting of $(CH_3O)_3Si(CH_2)_3N(CH_3)_2$, $(CH_3O)_3Si(CH_2)_3N(CH_2CH_2)_2$, $(CH_3O)_3Si(CH_2)_3N(CH_2CH_2CH_3)_2$, $(CH_3O)_3Si(CH_2)_4N(CH_3)_2$, and $(CH_3O)_3SiCH_2CH(CH_3)CH_2N(CH_3)_2$.

16. The composition of claim 13 wherein said cosurfactant is chosen from the group consisting of pentanol, hexanol, decanol, decanediol, glycerol, ethylene glycol, and propylene glycol.

17. The clear mixture of claim 13 wherein the silane is 3-(trimethoxysilyl)propyldidecylmethyl ammonium chloride (a) and the cosurfactant (b) is propylene glycol and (a) is present from 1 to 99 parts by weight, and (b) is present from 1 to 99 parts by weight.

18. The clear mixture of claim 13 wherein the silane is 3-(trimethoxysilyl)propyldidecylmethyl ammonium chloride (a) and the cosurfactant (b) is ethylene glycol and (a) is present from 1 to 99 parts by weight, and (b) is present from 1 to 99 parts by weight.

19. The clear mixture of claim 13 wherein the silane is 3-(trimethoxysilyl)propyldidecylmethyl ammonium chloride (a) and the cosurfactant (b) is pentanol and (a) is present from 1 to 99 parts by weight, and (b) is present from 1 to 99 parts by weight.

20. The clear mixture of claim 13 wherein the silane is 3-(trimethoxysilyl)propyldidecylmethyl ammonium chloride (a) and the cosurfactant (b) is a polyoxethylene glycol and (a) is present from 1 to 99 parts by weight, and (b) is present from 1 to 99 parts by weight.

21. The clear mixture of claim 13 wherein the silane is 3-(trimethoxysilyl)propyldidecylmethyl ammonium chloride (a) and the cosurfactant (b) is decanol and (a) is present from 1 to 99 parts by weight, and (b) is present from 1 to 99 parts by weight.

* * * * *